United States Patent [19]

Lay

[11] Patent Number: 5,374,276
[45] Date of Patent: Dec. 20, 1994

[54] EAR WAX REMOVER

[76] Inventor: Wuu P. Lay, Suite 1, 11F, No. 95-8 Chang Ping Rd. Sec. 1, Taichung, Taiwan R.O.C.

[21] Appl. No.: 191,627

[22] Filed: Feb. 4, 1994

[51] Int. Cl.⁵ .................... A45D 44/00; A61B 17/22
[52] U.S. Cl. .................................................. 606/162
[58] Field of Search .............................. 606/161, 162

[56] References Cited

U.S. PATENT DOCUMENTS

| | | | |
|---|---|---|---|
| 1,381,829 | 6/1921 | Hartman | 606/162 |
| 2,096,162 | 10/1936 | Daley | 606/162 |
| 4,353,364 | 10/1982 | Woods | 128/152 |
| 4,553,627 | 11/1985 | Gastmeier et al. | 181/135 |
| 4,707,318 | 11/1987 | Can | 264/138 |

FOREIGN PATENT DOCUMENTS

| | | | |
|---|---|---|---|
| 580729 | 7/1933 | Germany | 606/162 |
| 3633585 | 4/1988 | Germany | 606/162 |

*Primary Examiner*—Stephen C. Pellegrino
*Assistant Examiner*—Nancy Mulcare

[57] ABSTRACT

An ear wax remover comprises an elongate rod having an extractor head on a first end and a swab attachment portion on a second end. The extractor head has a generally mushroom shaped tip and a pair of frusto-conical projections extending annularly around the rod adjacent the tip. Both the tip and the two projections have frusto-conical recesses therearound which diverge in the direction of the second end of the rod. The peripheries of the tip and projections, and the recesses therein define engagement surfaces for the extraction of ear wax. The swab attachment portion has recessed helical lines which crisscross to define a hatching pattern for the wrapping securement of a cotton swab. A medical section of the rod is of enlarged diameter for ease of handling.

1 Claim, 2 Drawing Sheets

EAR WAX REMOVER

BACKGROUND OF THE PRESENT INVENTION

The present invention relates to an improved ear wax remover, and more particularly to an ear wax remover of the type comprising an elongate rod having an ear wax extracting element on one end thereof and, optionally, a fibrous cleaning member on the other end for removing particulate residues or detritus.

The extracting element in more conventional ear wax removers of the type generally comprises a hook like termination on the rod which is used to scrape out ear wax in an auditary canal. This implementation can prove problematical as the hook like appendage must be rotated to a proper orientation within the canal for effective operation, which is particularly difficult as the area is out of view of the user. More importantly, the sharp edges of the appendage could easily cause trauma to the auditory canal, or worse, to the tympanic membrane itself.

Whereas, the corresponding member in the ear wax remover of the present invention provides a non-directional scraping action which can be used at any orientation, and which provides a plurality of engagement surfaces for more effective action of ear wax and reduced likelihood of trauma.

Further, in lieu of the fixed fibrous cleaning member of more conventional devices, an attachment appendage is provided around which a cotton swab can be secured for cleaning of an auditary canal. The cotton swab is subsequently removed and discarded, providing a greater convenience over the more conventional fixed cleaning members which must be frequently washed for sanitation to be maintained. Moreover, the fixed cleaning member is prone to wear after repeated cleanings.

SUMMARY OF THE PRESENT INVENTION

An ear wax remover in accordance with the present invention comprises an elongate rod having an extractor head on a firm end and a swab attachment portion on a second end, with an enlarged diameter medical section for ease of handling. The extractor head has a generally mushroom shaped tip and a pair of frusto-conical projections extending annularly around the rod adjacent the tip. Both the tip and the two projections have annular, frusto-conical recesses around their undersides, which diverge in the direction of the second end of the rod. The peripheries of the tip and projections, and the recesses therein define multiple engagement surfaces for the extraction of ear wax. The swab attachment portion is defined by a hatching pattern of crisscrossing, recessed helical lines for enabling the wrapping securement of a cotton swab.

It is thus a main object of the present invention to provide an ear wax remover as characterized which affords greater convenience and effectiveness, and which reduces the danger of trauma to a user's ear.

It is a further object of the present invention to provide an ear wax remover as characterized, which affords greater sanitation and durability.

A thorough description of a preferred embodiment of the present invention is provided below along with accompanying drawings.

DETAILED DESCRIPTION OF THE PREFERRED EMBODIMENT

Figure 1:
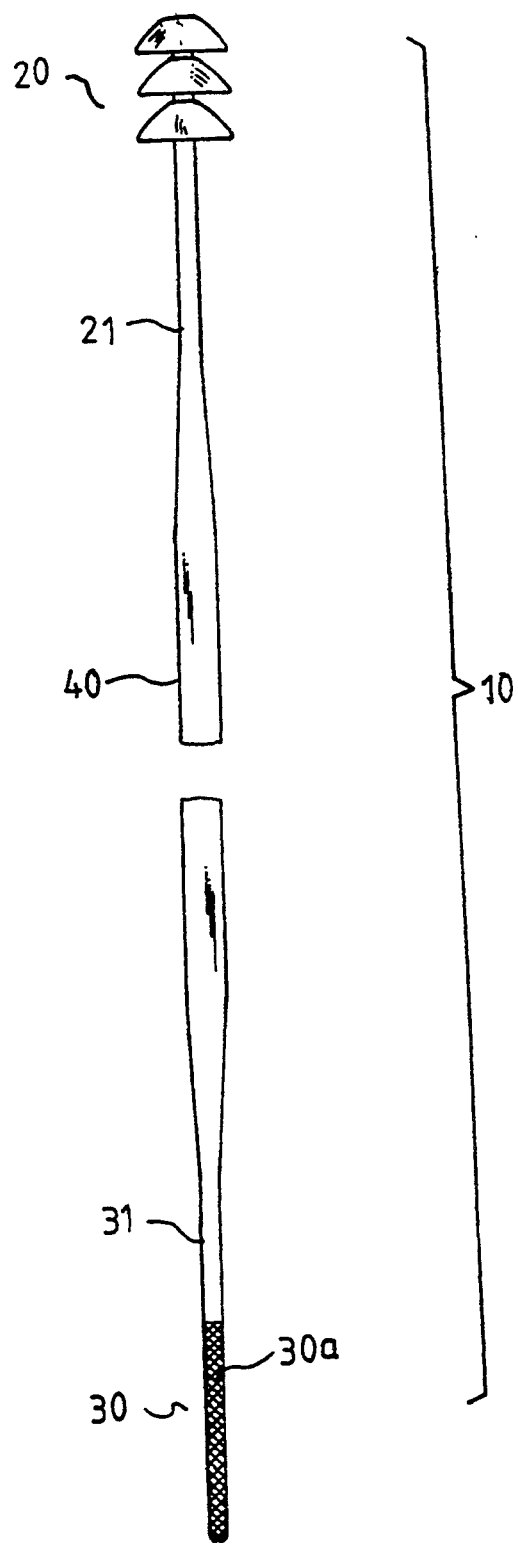
FIG. 1 is an elevational view showing tile ear wax remover of the present invention.

Referring to FIG. 1 of the drawings, the ear wax remover comprises a metal rod 10 which has been machined by an automatic lathe. On a first end is an extractor head 20, and on a second end is a swab attachment portion 30. An enlarged diameter medical section 40 of the rod adjoins with a lesser diameter shank 21 via a taper on one end thereof, and similarly adjoins with a second shank 31 on the other end. Shanks 21,31 adjoin respectively with head 20 and attachment portion 30.

Figure 2:
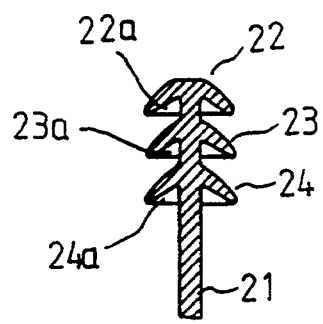
FIG. 2 is a sectional view of an extractor head on a first end of the ear wax remover.

Referring to FIG. 2, extractor head 20 has a generally mushroom shaped tip 22 formed on the terminal end of shank 21. Adjacent the tip 22 is a first projection 23 which extends radially outward around the shank 21 and diverges in the direction of the second end of the rod, so as to have the shape of a frustum of a cone. A similarly shaped second projection 24 is formed around shank 21 adjacent tile second projection, with both having an outer diameter approximately equal with that of tip 22. The tip 22 and the first and second projections 23,24 have respective annular recesses 22a,23a, and 24a formed therein which extend around shank 21 facing the second end thereof. The outer peripheries of the tip and projections, along with the generally frusto-conical recesses therein, define a plurality of engagement surfaces for the extraction of ear wax from an auditory canal.

Figure 3:
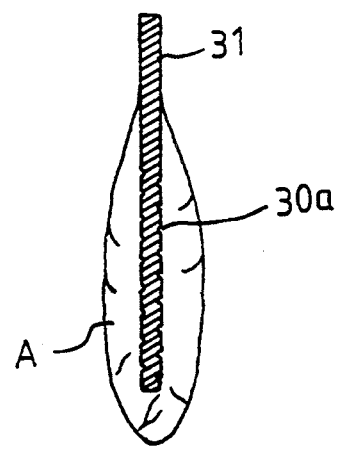
FIG. 3 is a sectional view of a swab attachment portion on the second end of the ear wax remover with a cotton swab wrapped therearound.

Referring to FIG. 3, the swab attachment portion 30 is defined by recessed spiral lines 30a, shown also in FIG. 1, formed around a portion of shank 31 and extending to the terminal end thereof. The spiral lines crisscross to form a hatching pattern which enables the wrapping securement of a cotton swab A for cleaning of an auditary canal. After use, the cotton swab A is simply removed and discarded. This feature provides a more sanitary instrument in comparison with the fixed cleaning devices found on more conventional ear wax removers which would have to be washed after each usage.

Note that as the engagement surfaces extend radially around shaft 21 in all directions there is no preferred orientation within an auditary canal for effective extraction of ear wax, as is the case with the more conventional hook like instruments. Moreover, the plurality of engagement surfaces provides more efficient traction of irregularly shaped ear wax, and better distributes applied pressure within an auditary canal so as to increase user comfort and reduce the possibility of trauma. Yet further, the rounded convex terminal face of tip 22 reduces further the likelihood of trauma to the tympanic membrane within an auditary canal should contact occur.

I claim:

1. An ear wax remover comprising a rod having:
a first section including a first end of said rod;
a second section including a second end of said rod;

a medial section of larger diameter than the first section or second section;

a generally mushroom shaped tip on the first end of said rod, said tip having an annular frustoconical first recess extending around the adjoining first section;

a first projection extending radially around the first section adjacent said tip, said first projection having a frustoconical shape which diverges towards the second end of said rod, and defining an annular frustoconical second recess extending around the adjoining first section;

a second projection extending radially around the first section adjacent said first projection, said second projection having a frustoconical shape which diverges towards the second end of said rod, and defining an annular frustoconical third recess extending around the adjoining first section, an attachment portion on the second section extending to the second end of said rod, and having recessed lines thereon defining a spiral hatching pattern for the wrapping securement of a cotton swab.

* * * * *